United States Patent [19]
Gross

[11] B 3,988,307

[45] Oct. 26, 1976

[54] SOLID PHASE SYNTHESIS OF PEPTIDES WITH CARBOXYL-TERMINAL AMIDES

[75] Inventor: Erhard Gross, Bethesda, Md.

[73] Assignee: The United States of America as represented by the Secretary of the Department of Health, Education and Welfare, Washington, D.C.

[22] Filed: Sept. 6, 1974

[21] Appl. No.: 503,817

[44] Published under the second Trial Voluntary Protest Program on January 13, 1976 as document No. B 503,817.

[52] U.S. Cl. .................. 260/112.5 R; 260/112.5 TR
[51] Int. Cl.² .................. C07C 103/52; C07G 7/00
[58] Field of Search ................................ 260/112.5

[56] References Cited
UNITED STATES PATENTS

| | | | |
|---|---|---|---|
| 3,732,199 | 5/1973 | Schwarz | 260/112.5 |
| 3,743,628 | 7/1973 | Bodanszky et al. | 260/112.5 |
| 3,775,378 | 11/1973 | Dahlmans et al. | 260/112.5 |
| 3,819,607 | 6/1974 | Heuser et al. | 260/112.5 |

*Primary Examiner*—Lewis Gotts
*Assistant Examiner*—Reginald J. Suyat
*Attorney, Agent, or Firm*—John S. Robert, Jr.; Norman J. Latker; Thomas G. Ferris

[57] ABSTRACT

The method of utilizing $\alpha,\beta$-unsaturated amino acids, acyl, and N-acyl derivatives as linking agents in the solid phase synthesis of peptides with the corresponding production of carboxyl terminal amides. Preferred unsaturated amino acids are dehydroalanine and dehydrobutyrine which are constituents in naturally occurring amides such as nisin and subtilin. The synthesis follows conventional lines of R. B. Merrifield et al including blocking of the amino nitrogen, with the exception that the release agent contains an amount of water equimolar to the reactant $\alpha,\beta$-unsaturated amino acid.

10 Claims, No Drawings

SOLID PHASE SYNTHESIS OF PEPTIDES WITH CARBOXYL-TERMINAL AMIDES

The present invention relates to the utilization of $\alpha,\beta$-unsaturated amino acids such as dehydroalanine in the solid phase synthesis of peptides wherein said unsaturated acids fill the roll of establishing the link to the solid support. Also, on release the presence of the unsaturated amino acids provides a modus for incorporation of carboxyl terminal amides in the peptide chain. $\alpha,\beta$-unsaturated amino acids suitable for utilization in the present invention include dehydroalanine, dehydrobutyrine ($\beta$-methyldehydroalanine), dehydroserine, dehydroleucine, dehydrophenylalanine, dehydrotryptophan, dehydroarginine, dehydroproline, dehydrovaline, and dehydrocysteine (cf. *Handbook of Biochemistry*, 2d Edition, Silber, ed., The Chemical Rubber Co., Cleveland, Ohio, 1970, page B-50). The stability of the $\alpha,\beta$-unsaturated amino acid is improved by N-acylation or N-amino acylation and the utilization of acyl derivatives such as Boc (tert-butyloxycarbonyl) and related compounds is preferred (cf. E. Gross. *Handbook of Biochemistry*, page B-50, above).

PRIOR ART

General Prior Art

1. R. B. Merrifield, "Solid-Phase Peptide Synthesis," *Advances in Enzymology*, 32, 1969, 221–295.
2. Bodanszky and Ondetty, *Peptide Synthesis*, Interscience Wiley, 1967.
3. Stewart and Young, *Solid-Phase Peptide Synthesis*, W. H. Freeman and Co., San Francisco, 1969.

Specific Prior Art

1. E. Gross, et al, *Angewandte Chemie*, 12, August 1973, pages 664–665 (English Edition).
2. E. Gross, et al, *Angewandte Chemie*, 85, January 1973, pages 672–673 (German Edition).
3. E. Gross and J. L. Morell, *J. Amer. Chem. Soc.*, 93, 4634 (1971).
4. E. Gross et al, *Proc. Nat. Acad. Sci USA*, 62, 952 (1969).
5. E. Gross in J. Meienhofer, *Chemistry and Biology of Peptides*, Proceedings of the 3rd American Peptide Symposium, Ann Arbor Science Publishers, Ann Arbor, Michigan, 1972, page 671.

Merrifield, ante, at page 223 defines solid-phase peptide synthesis as follows, "solid-phase peptide synthesis is based on the idea that a peptide chain can be assembled in a step-wise manner while it is attached at one end to a solid support. With the growing chain covalently anchored to an insoluble particle at all stages of the synthesis, the peptide will also be completely insoluble, and furthermore it will be in a suitable physical form to permit rapid filtration and washing."

The present invention follows the format of the prior art as to solid-phase peptide synthesis with the exception of utilization of $\alpha,\beta$-unsaturated amino acids as the link to the support and the utilization of an aqueous release agent as opposed to the conventional organic for the reaction of the double bond with water and consequent production of a terminal carboxy amide product.

GENERALIZED DESCRIPTION OF THE SOLID-PHASE SYNTHESIS WITH $\alpha,\beta$-UNSATURATED AMINO ACIDS AS LINKING AGENT The solid-phase synthesis has been again described by Stewart et al, page 3 (ante), as a "special case of stepwise synthesis of peptides from the C-terminus (the carboxyl end of the peptide). The linkage of the C-terminal amino acid to the resin is, in effect, a substituted benzyl ester, and the chemistry of solid-phase synthesis is essentially that used in the step-wise synthesis of a peptide benzyl ester in solution."

THE SUPPORT

An insoluble polymeric support is conventional in the solid-phase peptide syntheses and a preferred polymer is a copolymer of styrene of 2 percent divinylbenzene (DVB) in bead form which has been further modified by chloromethylation. Also utilizable is an insoluble hydroxy methyl resin or polymer (Stewart et al, page 9, ante).

THE LINKING AGENT

The solid support above is made to react with the carboxyl group of the $\alpha,\beta$-unsaturated amino acid in such a way that the amino acid is bound covalently to the polymer. During this step the amine group of the amino acid is covered or protected or blocked with a protecting group as, for example, with a Boc group (t-butyloxycarbonyl) so that the amine will not react with the polymer. Also utilizable as a protecting group is carbobenzoxy (benzyloxycarbonyl) (cf. Stewart et al, page 13, ante) and t-amyloxycarbonyl group (cf. Stewart et al, page 16, ante). The blocking or protecting group is selected so that it can be removed without damage to the bond holding the amino acid to the support. After removal of this protecting group, a second N-protected amino acid can be caused to acylate the exposed amine group of the first amino acid, thus forming the first peptide bond. At each stage, to assist in the linking of the support to the first amino acid, in this case $\alpha,\beta$-unsaturated amino acid, a coupling agent is utilized. A preferred coupling agent is DCC (dicyclohexylcarbodiimide).

CLEAVAGE OF THE FINISHED PEPTIDE FROM THE RESIN

Historically, the preferred cleavage reagent has been organic consisting of 1 N HCl in glacial acetic acid but due to the equivalent amount of water to starting amine necessary for the formation of the peptide amide, the release agent in this case becomes aqueous rather than organic and results in the simultaneous removal of the peptide from the solid support and the conversion of the $\alpha,\beta$-unsaturated amino acid to amide and keto acid.

The present method has advantages over other methods for the synthesis of peptide amides by being applicable under milder conditions and free from undesirable side reactions. Further, $\alpha,\beta$-unsaturated amino acids, such as dehydroalanine and dehydrobutyrine have been found to be constituents of naturally occurring peptides, nisin and subtilin. These exemplary unsaturated amino acids are formed under conditions of $\beta$-elimination and formation of the double bond from corresponding saturated acid. Further, the biologically active tripeptide pyroglutamylhistidylproline amide (thyrotropin-releasing factor, TRF) was synthesized (see below) utilizing a substituted dehydroalanine linking agent.

As exemplary of the synthesis utilized, the α,β-unsaturated amino acid dehydroalanine $H_2C=CNHR—COOH$, R = acyl or aminoacyl, may be employed in various ways in the solid phase synthesis of peptides. It may, for instance, act as vehicle for the attachment of peptides to insoluble supports and/or donate its nitrogen to amide groups. The latter occurs under acidic conditions in the presence of equimolar ratios of water and may be invoked once the desired number of amino acid residues has been added to the growing peptide chain.

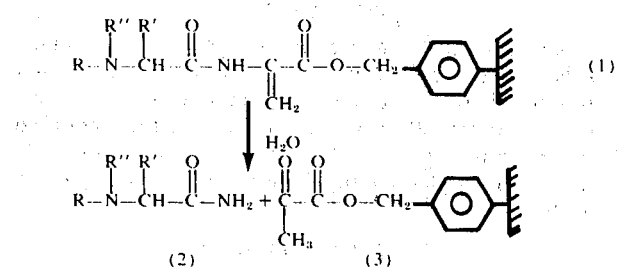

R = Boc; R' = R" = H (1a)
R = Boc-leucylalanyl, R' = R" = H (1b)
R = Boc; R'—R" = —$CH_2$—$CH_2$—$CH_2$— (1c)
R = Boc-pyroglutamylhistidyl, R'—R" = —$CH_2$—$CH_2$—$CH_2$— (1d)
R = leucylalanyl, R' = R" = H (2a)
R = pyroglutamylhistidyl, R'—R" = —$CH_2$—$CH_2$—$CH_2$— (2b)

The model peptide leucylalanylglycine amide and the thyrotropin-releasing factor (TRF), pyro-L-glutamyl-L-histidyl-L-proline amide (L-5-oxo-2-pyrrolidinylcarbonyl-L-histidyl-L-prolinamide) were synthesized in order to test the utility of this novel route to peptide amides.

EXAMPLE 1

Boc-glycyldehydroalanine (Boc = tert-butyloxycarbonyl) [m.p. 157°–159°C, decomp., $\lambda_{max}$ ($CH_3OH$) = 241 nm ($\epsilon$= 5560); Gly 1.00; $NH_3$ 1.03], prepared in 84% yield from Boc—glycyl—O—tosylserine methyl ester by β-elimination, was coupled to the chloromethylated (1.25 mmol Cl/g) styrene-2% divinylbenzene copolymer in dimethylformamide in the presence of triethylamine (40°C; 48 h) to give the peptide resin (1a) (0.41 mmol Boc—dipeptide/g).

EXAMPLE 2

Boc-leucylalanylglycyldehydroalanine resin (1b) was obtained after two successive cycles of solid phase synthesis with Boc—amino acids under the reaction conditions given in Example 7. Treatment of (1b) in the presence of 1 equivalent of water with 1 N hydrogen chloride in glacial acetic acid for 30 min at 50°C resulted in a. the cleavage of the dehydroalanine residue with formation of the amide (2a) and the pyruvyl resin (3);
b. the simultaneous removal of the Boc-protecting group from the $H_2N$-terminus.

EXAMPLE 3

Leucylalanylglycine amide (2a) was solidified by trituration in ethyl ether. Crystallization from methanol/ethyl ether gave a product (91% yield) which showed single spots and the given $R_f$ values upon thin layer chromatography on silica gel in the following solvent systems: A 0.14, B 0.62, C 0.35; Gly 1.00, Ala 0.98, Leu 1.00, $NH_3$ 0.98. Elemental analysis gave the expected values.

EXAMPLE 4

Boc-prolyldehydroalanine [m.p. 154°–156°C; $\lambda_{max}$ ($CH_3OH$) = 240 nm ($\epsilon$ = 5,300); Pro 1.00, $NH_3$ 1.01], obtained in 59% yield from Boc—prolyl—O—tosylserine methyl ester under the conditions of β-elimination, was coupled (25°C; 48 h) to the chloromethylated (2.3 mmol Cl/g) styrene-2% divinylbenzene copolymer as described for (1a) to give the Boc-prolyldehydroalanine resin (1c) (0.51 mmol of Boc-dipeptide/g).

EXAMPLE 5

Boc-pyroglutamylhistidylprolyldehydroalanine resin (1d) was synthesized according to the procedure given for (1b) using Boc—amino acids in the coupling steps.

EXAMPLE 6

Pyroglutamylhistidylproline amide (TRF) (2b) was isolated after treatment of (1d) with 1 equivalent of water in 1 N hydrogen chloride in glacial acetic acid as specified for (2a). A minor contamination was removed by partition chromatography on silica gel in the solvent system chloroform/methanol = 1:1. The purified tripeptide amide (TRF) gave single spots and the given $R_f$ values upon thin layer chromatography in the following solvent systems: A 0.03, B 0.46, D 0.27, E 0.27; Glu 1.00, Pro 1.02, His 0.99, $NH_3$ 1.00; $[\alpha]_D^{20}$ = −45.1 (c 0.25 glacial acetic acid); yield 63%.

The biological activities of (2b) and another sample of synthetic TRF (Abbott Laboratories, North Chicago, Illinois) were compared in the mouse bioassay. Potency estimates and 95% confidence limits (C.L.) were calculated by the methods of Brownlee (Statistical Theory and Methodology in Science and Engineering, John Wiley, 1960, page 294) and Finney (Statistical Methods in Biological Assay, Charles Griffin, London, 1964, page 370), respectively. One nanogram of TRF synthesized on the dehydroalanine resin was equivalent to 1.2 nanograms (95% C.L. 0.67–2.20 ng) of the reference preparation.

EXAMPLE 7

Solid Phase Synthesis of Peptides Attached to the Support Via Dehydroalanine

| Synthesis Step | Time (min) |
|---|---|
| 1. $CH_2Cl_2$ wash (4×) | 1.5 |
| 2. 25% TFA—$CH_2Cl_2$ prewash (1×) | 1.5 |
| 3. 25% TFA—$CH_2Cl_2$ deprotection (1×) | 30.0 |
| 4. $CH_2Cl_2$ wash (5×) | 1.5 |
| 5. 10% $NEt_3$—$CH_2Cl_2$ prewash (1×) | 1.5 |
| 6. 10% $NEt_3$—$CH_2Cl_2$ neutralization (1×) | 10.00 |
| 7. $CH_2Cl_2$ wash (5×) | 1.5 |
| 8. Boc—AA—$CH_2Cl_2$ (1×) | 10.0 |
| 9. DCC—$CH_2Cl_2$ (1×) | 180.0 |
| 10. $CH_2Cl_2$ wash (3×) | 1.5 |
| 11. EtOH wash (3×) | 1.5 |

Boc-amino acids and DCC were used in fivefold excess.

TFA = trifluoroacetic acid
$NEt_3$ = triethylamine
Boc = tert-butyloxycarbonyl
DCC = dicyclohexylcarbodiimide
AA = amino acid The experimental protocol above is similar to that shown in Stewart et al, ante, entitled "Schedule A for Solid Phase Peptide Synthesis Diimide Coupling," at page 38.

What is claimed is:

1. A method of synthesizing peptides by solid phase procedure which comprises attaching an $\alpha,\beta$-unsaturated amino acid through the teriminal carboxyl group to a solid insoluble support with the $\alpha$-nitrogen blocked by a protecting group and subsequently unblocking the $\alpha$-nitrogen by removing said protecting group and growing the peptide chain on said support by sequentially adding amino acids conforming to the desired peptide sequence and adding an acidic aqueous release solution to said peptide and support to convert the $\alpha,\beta$-unsaturated amino acid to a carboxyl terminal amide and releasing said amide from said solid support.

2. The method according to claim 1 wherein the aqueous release solution contains an amount of water equimolar to the amount of $\alpha,\beta$-unsaturated amino acid utilized.

3. The method according to claim 1 wherein the aqueous release solution is a mixture of 1 N HCl in glacial acetic acid.

4. The method according to claim 1 used for the synthesis of pyroglutamylhistidylproline amide (Thyrotropin-releasing factor; TRF) by
   a. attaching Boc-prolyldehydroalanine to the solid support;
   b. removing the Boc-group by treatment with 25% TFA in $CH_2Cl_2$;
   c. attaching Boc-histidine and Boc-pyroglutamic acid via solid phase techniques of peptide synthesis using dicyclohexylcarbodiimide as activating agent and removing the Boc-group from histidine by treatment with 25% TFA in $CH_2Cl_2$;
   d. removing pyroglutymylhistidylproline amide (TRF) from the solid support by treatment with one equivalent of water in 1 N HCl in glacial acetic acid.

5. The method according to claim 1 wherein the protecting group is Boc.

6. The method according to claim 1 wherein the support is chloromethylated styrene/DVB copolymer.

7. The method according to claim 1 wherein the support is hydroxymethylated styrene/DVB copolymer.

8. The method according to claim 1 wherein the $\alpha,\beta$-unsaturated amino acid is selected from the group consisting of dehydroalanine, dehydrobutyrine ($\beta$-methyldehydroalanine), dehydroserine, dehydroleucine, dehydrophenylalanine, dehydrotryptophan, dehydroarginine, dehydroproline, dehydrovaline, and dehydrocysteine.

9. The method according to claim 8 wherein the $\alpha,\beta$-unsaturated amino acid is dehydroalanine.

10. The method according to claim 8 wherein the $\alpha,\beta$-unsaturated amino acid is dehydrobutyrine.

* * * * *